United States Patent [19]

Frei et al.

[11] Patent Number: 4,959,386
[45] Date of Patent: Sep. 25, 1990

[54] PESTICIDES

[75] Inventors: Bruno Frei, Liestal, Switzerland; Hari B. Mereyala, Pune, India; Anthony C. O'Sullivan, Basel, Switzerland; Kazuo Sato; Toshiaki Yanai, both of Kanagawa, Switzerland

[73] Assignee: Ciba-Geigy Corporation, Ardsley, N.Y.

[21] Appl. No.: 252,031

[22] Filed: Sep. 28, 1988

Related U.S. Application Data

[63] Continuation of Ser. No. 18,688, Feb. 25, 1987, abandoned, which is a continuation of Ser. No. 807,580, Dec. 11, 1985, abandoned.

[30] Foreign Application Priority Data

Dec. 14, 1984 [CH] Switzerland ............... 5940/84
May 30, 1985 [CH] Switzerland ............... 2289/85

[51] Int. Cl.$^5$ ................ A61K 31/365; C07D 315/00
[52] U.S. Cl. ............................. 514/450; 549/264
[58] Field of Search ................... 549/264; 514/450

[56] References Cited

U.S. PATENT DOCUMENTS

| | | | |
|---|---|---|---|
| 4,093,629 | 6/1978 | Fisher | 549/264 |
| 4,134,973 | 1/1979 | Fisher et al. | 514/30 |
| 4,156,720 | 5/1979 | Fisher et al. | 514/30 |
| 4,199,569 | 4/1980 | Chabala et al. | 514/30 |
| 4,201,861 | 5/1980 | Mrozik et al. | 536/7.1 |
| 4,206,205 | 6/1980 | Mrozik et al. | 514/30 |
| 4,423,209 | 12/1983 | Mrozik | 536/7.1 |
| 4,457,920 | 7/1984 | Mrozik | 549/264 |
| 4,469,682 | 9/1984 | Mrozik | 549/264 |
| 4,587,247 | 5/1986 | Linn et al. | 549/264 |

FOREIGN PATENT DOCUMENTS

| | | | |
|---|---|---|---|
| 0001689 | 5/1979 | European Pat. Off. | 549/264 |
| 0074758 | 3/1983 | European Pat. Off. | 549/264 |

Primary Examiner—Glennon H. Hollrah
Attorney, Agent, or Firm—Edward McC. Roberts

[57] ABSTRACT

The present invention relates to novel compounds of the formula

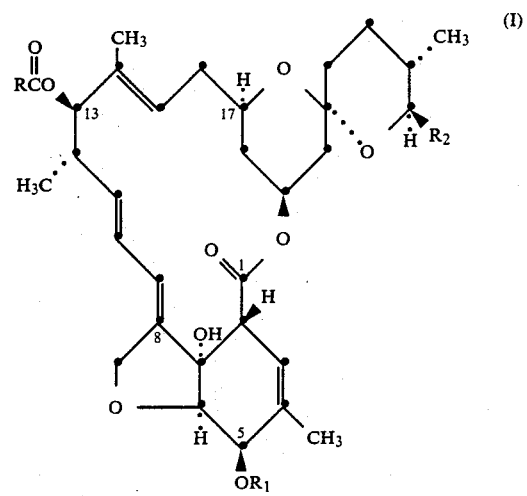

wherein
$R_1$ is hydrogen, a silyl group or an acyl group,
$R_2$ is methyl, ethyl, is propyl or sec-butyl, and R is hydrogen, unsubstituted or substituted straight chain or branched $C_1$–$C_{18}$alkyl, an unsubstituted or substituted cycloaliphatic group containing 3 to 10 carbon atoms, unsubstituted or substituted $C_2$–$C_6$alkenyl, unsubstituted or substituted $C_2$–$C_6$-alkynyl, unsubstituted or substituted phenyl or unsubstituted or substituted benzyl. These compounds posseses advantageous pesticidal properties and are suitable in particular for controlling pests in agriculture and the storage sector.

7 Claims, No Drawings

PESTICIDES

This application is a continuation of application Ser. No. 018,688, filed Feb. 25, 1987, now abandoned, which is a continuation of application Ser. No. 807,580, filed Dec. 11, 1985, now abandoned.

The present invention relates to novel 13$\beta$-milbemycin derivatives of formula I, to the preparation thereof and to the use thereof for controlling pests, as well as to pesticidal compositions which contain as active ingredient at least one of these compounds.

The novel compounds are of the general formula I wherein
R$_1$ is hydrogen, a silyl group or an acyl group,
R$_2$ is methyl, ethyl, isopropyl or sec-butyl, and
R is hydrogen, unsubstituted or substituted straight chain or branched C$_1$-C$_{18}$alkyl, an unsubstituted or substituted cycloaliphatic group containing 3 to 10 carbon atoms, unsubstituted or substituted C$_2$-C$_6$alkenyl, unsubstituted or substituted C$_2$-C$_6$alkynyl, unsubstituted or substituted phenyl or unsubstituted or substituted benzyl.

Preferred meanings are: unsubstituted or halogenated C$_1$-C$_8$alkyl; C$_3$-C$_6$cycloalkyl which is unsubstituted or substituted by one or more methyl groups; adamantyl; unsubstituted or halogenated C$_2$-C$_6$alkenyl and C$_2$-C$_6$alkynyl.

Possible substituents of the alkyl, cycloalkyl, alkenyl and alkynyl groups are for example 1 to 7 halogen atoms or 1 to 6 C$_1$-C$_6$alkoxy groups and possible substituents of the phenyl and benzyl groups are 1 to 3 substituents selected from the group consisting of halogen atoms, C$_1$-C$_6$alkyl, C$_1$-C$_4$alkylthio and nitro. A further possible substituent of the alkyl group directly attached to the carboxylic acid radical is an unsubstituted or substituted phenoxy group, e.g. a halogenated phenoxy group, preferably a phenoxy group which is substituted by 1 to 3 halogen atoms. The cycloalkyl groups may also be substituted by C$_1$-C$_4$alkyl groups.

Depending on the number of carbon atoms indicated, alkyl as substituent or as moiety of a substituent will be understood as meaning for example the following groups: methyl, ethyl, propyl, butyl, pentyl, hexyl, heptyl, octyl, nonyl or decyl, as well as the isomers thereof, e.g. isopropyl, isobutyl, tert-butyl or isopentyl. Haloalkyl is a mono- to perhalogenated alkyl substituent, e.g. CHCl$_2$, CHF$_2$, CH$_2$Cl, CCl$_3$, CF$_3$, CH$_2$F, CH$_2$CH$_2$Cl, CHBr$_2$. Throughout this specification, halogen will be understood as meaning fluorine, chlorine, bromine or iodine, with fluorine, chlorine or bromine being preferred. Suitable cycloaliphatic groups are mono- to tetracyclic groups, e.g. cyclopropyl, cyclobutyl, cyclopentyl, cyclohexyl, Decalin, hydrindane, bicycloheptane, bicyclooctane, norbornane, bornane or adamantyl. Said cycloaliphatic groups are preferably unsubstituted or substituted by one or more methyl groups. Alkenyl is an aliphatic, acyclic hydrocarbon radical characterised by at least one C=C double bond, e.g. vinyl, propen-1-yl, allyl, buten-1-yl, buten-2-yl or buten-3-yl. Haloalkenyl is therefore such an alkenyl radical which is substituted by one or more halogen atoms. Alkynyl is a straight or branched carbon chain which is characterised by at least one C≡C triple bond. Typical representatives are for example ethynyl, propion-1-yl, propargyl or butyn-1-yl. Alkoxyalkyl is an unbranched or branched alkyl group which is interrupted by an oxygen atom, e.g. CH$_2$OCH$_3$, CH$_2$CH$_2$OCH$_3$, CH$_2$CH(CH$_3$)OCH$_3$, CH$_2$OC$_2$H$_5$, C(CH$_3$)$_2$OCH$_3$, CH$_2$OC$_3$H$_7$-i or CH$_2$CH$_2$CH$_2$OCH$_3$.

Substituted phenyl is for example 2,4-dichlorophenyl, 2,3,6-trichlorophenyl, p-bromophenyl, 2,4-xylyl, 3-nitrophenyl, 4-chloro-2-methylphenyl, 4-methyl-2-methoxyphenyl, 2,4,6-trimethylphenyl or p-methylthiophenyl.

Without any restrictions being implied, R is for example hydrogen, methyl, ethyl, propyl, isopropyl, n-butyl, sec-butyl, tert-butyl, neopentyl, chloromethyl, trifluoromethyl, trichloromethyl, trichloroethyl, trichloro-tert-butyl, 1,2,2,2-tetrachloroethyl, 1,3,3,3-tetrachloropropyl, 3-chloropropyl, ethenyl, propenyl, propynyl, methoxymethyl, isopropoxymethyl, 1-methyl-1-methoxyethyl, 2,2-dimethylvinyl, 1,2,2-trichlorovinyl, 1,3,3,3-tetrachloropropyl, 1,1-dichloro-2,2,2-trifluoroethyl, 1,3-pentadienyl, ethynyl, propyn-1-yl, butyn-1-yl, cyclopropyl, 2,2-dimethylcyclopropyl, 1-methylcyclopropyl, 2,2-dimethyl-3-(2,2-dichlorovinyl)cyclopropyl, cyclobutyl, cyclopentyl, cyclohexyl, adamantyl, phenyl, benzyl, p-tolyl, p-chlorophenyl, 2,6-dichlorophenyl or 2,4-dinitrophenyl or 4-fluorophenoxymethyl.

Compounds of formula I wherein R$_1$ is hydrogen are preferred. Acyl and silyl groups R$_1$ will in general be understood as being protecting groups. Examples of suitable acyl groups are the radicals R$_5$—C(O)—, wherein R$_5$ is C$_1$-C$_{10}$alkyl, C$_1$-C$_{10}$haloalkyl, or a phenyl or benzyl radical which is unsubstituted or substituted by substituents selected from the group consisting of halogen, C$_1$-C$_3$alkyl, C$_1$-C$_3$-haloalkyl, C$_1$-C$_3$alkoxy, C$_1$-C$_3$haloalkoxy, cyano and nitro, with the preferred meanings of R$_5$ being C$_1$-C$_6$alkyl, C$_1$-C$_6$haloalkyl, or phenyl which is unsubstituted or substituted by halogen, C$_1$-C$_3$alkyl, CF$_3$ or nitro. The acetyl group is particularly preferred. An example of an acyl compound is 5-O-acetyl-13$\beta$-formyloxymilbemycin A$_4$. Suitable silyl groups R$_1$ are the radicals —Si(R$_6$)(R$_7$)(R$_8$), wherein R$_6$, R$_7$ and R$_8$, preferably independently of one another, are C$_1$-C$_4$alkyl, benzyl or phenyl and form for example one of the groups trimethylsilyl, diphenyl-tert-butylsilyl, bis(isopropyl)methylsilyl or triphenylsilyl or, preferably, tert-butyldimethylsilyl.

Throughout this specification, compounds wherein R$_2$ is sec-butyl shall likewise be regarded as belonging to the class of milbemycin derivatives although according to conventional classification they are derived from avermectin derivatives. However, avermectin aglycons (carrying an OH group in the 13α-position) can be converted into milbemycin homologues in accordance with U.S. Pat. No. 4,173,571.

In naturally occurring milbemycins ($R_1 = H$; $R_2 = CH_3$, $C_2H_5$ or $isoC_3H_7$), in place of the ester group of the compounds of formula I of this invention, the substituent in the 13-position is always hydrogen, as the following formula shows:

[Chemical structure diagram]

$R_2 = CH_3$: milbemycin $A_3$
$R_2 = C_2H_5$: milbemycin $A_4$
$R_2 = isoC_3H_7$: milbemycin D
$R_2 = sec-C_4H_9$: 13-deoxy-22,23-dihydro-C-076-Bla-aglycon.

However, in avermectins an α-L-oleandrosyl-α-L-oleandrose radical which is attached through oxygen in the α-configuration to the macrolide molecule is in the 13-position. Moreover, avermectins differ structurally from milbemycins by the presence of a 23-OH group or $\Delta^{22,23}$ double bond and, usually, by the presence of a substituent $R_2 = sec-C_4H_9$. By hydrolysing the sugar residue of avermectins, the corresponding avermectinaglycons containing a 13α-hydroxy group which is adjacent to a C=C double bond are readily obtained. As stated above, avermectinaglycons can be converted into milbemycin homologues. In the milbemycin derivatives of the present invention, the $\Delta^{22,23}$ double bond always occurs in hydrogenated form and the substituent in the 13 position is always β-oriented.

On account of their pronounced parasiticidal and insecticidal activity, the following subgroups of compounds of formula I are particularly preferred:

Group Ia:
Compounds of formula I, wherein $R_1$ is hydrogen, $R_2$ is methyl, ethyl, isopropyl or sec-butyl and R has the following meanings:
hydrogen, or $C_1$-$C_6$alkyl, $C_2$-$C_4$alkenyl, $C_2$-$C_4$alkynyl or $C_3$-$C_6$cycloalkyl, each unsubstituted or substituted by 1 to 4 halogen atoms or $C_1$-$C_4$alkoxy;
phenyl which is unsubstituted or substituted by 1 to 3 substituents selected from the group consisting of halogen, $C_1$-$C_4$alkyl, $C_1$-$C_4$alkoxy, $C_1$-$C_4$alkylthio and nitro.

Group Ib:
Compounds of formula I, wherein $R_1$ is hydrogen, $R_2$ is methyl, ethyl, isopropyl or sec-butyl and R has the following meanings:
hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or methoxy;
phenyl which is unsubstituted or substituted by chlorine, fluorine, $C_1$-$C_2$alkyl, $C_1$-$C_2$alkoxy, $C_1$-$C_2$alkylthio or nitro.

Group Ic:
Compounds of formula I, wherein $R_1$ is hydrogen, $R_2$ is methyl or ethyl and R has the following meanings:
hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or methoxy;
phenyl which is unsubstituted or substituted by chlorine, fluorine, $C_1$-$C_2$alkyl, $C_1$-$C_2$alkoxy, $C_1$-$C_2$alkylthio or nitro.

Group Id:
Compounds of formula I, wherein $R_1$ is hydrogen, $R_2$ is isopropyl or sec-butyl and R has the following meanings:
hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 4 chlorine or fluorine atoms or methoxy;
phenyl which is unsubstituted or substituted by chlorine, fluorine, $C_1$-$C_2$alkyl, $C_1$-$C_2$alkoxy, $C_1$-$C_2$alkylthio or nitro.

Group Ie:
Compounds of formula I, wherein $R_1$ is hydrogen, $R_2$ is methyl, ethyl, isopropyl or sec-butyl and R has the following meanings:
hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or methoxy;
phenyl which is unsubstituted or substituted by chlorine, fluorine, $C_1$-$C_2$alkyl, $C_1$-$C_2$alkoxy, $C_1$-$C_2$alkylthio or nitro.

Group If:
Compounds of formula I, wherein $R_1$ is hydrogen, $R_2$ is methyl or ethyl and R has the following meanings:
hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or methoxy;

Group Ig:
Compounds of formula I, wherein $R_1$ is hydrogen, $R_2$ is isopropyl or sec-butyl and R has the following meanings:
hydrogen, or $C_1$-$C_4$alkyl, $C_2$-$C_3$alkenyl, $C_2$-$C_3$alkynyl or $C_3$-$C_6$cycloalkyl, each unsubstituted or substituted by 1 to 3 chlorine or fluorine atoms or methoxy;

Group Ih:
Compounds of formula I, wherein $R_1$ is hydrogen, $R_2$ is ethyl or isopropyl and R has the following meanings:
hydrogen; $C_1$-$C_8$alkyl which is unsubstituted or monosubstituted by $C_1$-$C_4$alkoxy or by mono- to trihalogenated phenoxy or substituted by 1 to 5 halogen atoms; or a mono- to tetracyclic aliphatic group which contains a total of 3 to 10 carbon atoms in the ring or ring system and which is unsubstituted or substituted by one or more substituents selected from the group consisting of $C_1$-$C_4$alkyl and halogenated $C_2$-$C_4$alkenyl; or mono- to trihalogenated $C_2$-$C_4$alkenyl; $C_3$-$C_4$alkynyl; or phenyl which is substituted by 1 to 3 substituents selected from the group consisting of halogen, $C_1$-$C_4$alkyl and nitro.

Group Ii:

Compounds of formula I, wherein $R_1$ is hydrogen, $R_2$ is ethyl or isopropyl and R has the following meanings: hydrogen; $C_1$–$C_8$alkyl which is unsubstituted or substituted by 1 to 3 substituents selected from the group consisting of chlorine and fluorine; or fluorophenoxymethyl; $C_3$–$C_4$cycloalkyl which is unsubstituted or substituted by a methyl group; or adamantyl, trichlorovinyl or monochlorophenyl.

Examples of particularly preferred 5-hydroxy derivatives of formula I are:
13β-formyloxymilbemycin D
13β-acetoxymilbemycin D
13β-pivaloyloxymilbemycin D
13β-formyloxymilbemycin $A_3$
13β-acetoxymilbemycin $A_3$
13β-pivaloyloxymilbemycin $A_3$
13β-formyloxymilbemycin $A_4$
13β-acetoxymilbemycin $A_4$
13β-pivaloyloxymilbemycin $A_4$.
13β-(2'-methoxy-2'-methylpropionyloxy)milbemycin D
13β-(2'-methoxy-2'-methylpropionyloxy)milbemycin $A_4$
13β-trichloroacetoxymilbemycin D
13β-(4'-chlorobutanoyloxy)milbemycin D
13β-trichloroacryloyloxymilbemycin D
13β-cyclopropanecarbonyloxymilbemycin D
13β-cyclobutanecarbonyloxymilbemycin D
13β-heptanoyloxymilbemycin D
13β-(3'-chloro-2'2'-dimethylpropionyloxy)milbemycin $A_4$
13β-(3'-chloro-2'2'-dimethylpropionyloxy)milbemycin D
13β-(1'-methylcyclopropanecarbonyloxy)milbemycin $A_4$
13β-(1'-methylcyclopropanecarbonyloxy)milbemycin D
13β-(1-adamantanecarbonyloxy)milbemycin D
13β-(p-fluorophenoxyacetoxy)milbemycin $A_4$
13β-(2'-chloro-2'-methylpropionyloxy)milbemycin $A_4$
13β-(2',2'-dichloropropionyloxy)milbemycin $A_4$
13β-(2',2'-dimethylbutanoyloxy)milbemycin $A_4$
13β-(3',3'-dimethylbutanoyloxy)milbemycin $A_4$
13β-(2',2',3',3'-tetramethylbutanoyloxy)milbemycin $A_4$
13β-(p-chlorobenzoyloxy)milbemycin $A_4$
13β-(3',3',3'-trifluoropropionyloxy)milbemycin $A_4$
13β-chloroacetoxymilbemycin $A_4$
13β-(2'-chloro-3',3',3'-trifluoropropionyloxy)milbemycin D
13β-(3',3',3'-trifluoropropionyloxy)milbemycin D.

Examples of preferred compounds of formula I carrying a protecting group at the 5-hydroxy group are:
5-O-tert-butyldimethylsilyl-13β-formyloxymilbemycin D
5-O-tert-butyldimethylsilyl-13β-acetoxymilbemycin D
5-O-tert-butyldimethylsilyl-13β-pivaloyloxymilbemycin D
5-O-tert-butyldimethylsilyl-13β-formyloxymilbemycin $A_3$
5-O-tert-butyldimethylsilyl-13β-acetoxymilbemycin $A_3$
5-O-tert-butyldimethylsilyl-13β-pivaloyloxymilbemycin $A_3$
5-O-tert-butyldimethylsilyl-13β-formyloxymilbemycin $A_4$
5-O-tert-butyldimethylsilyl-13β-acetoxymilbemycin $A_4$
5-O-tert-butyldimethylsilyl-13β-pivaloyloxymilbemycin $A_4$
5-O-tert-butyldimethylsilyl-13β-(2'-methoxy-2'-methylpropionyloxy)milbemycin D
5-O-tert-butyldimethylsilyl-13β-(2'-methoxy-2'-methylpropionyloxy)milbemycin $A_4$
5-O-tert-butyldimethylsilyl-13β-trichloroacetoxymilbemycin D
5-O-tert-butyldimethylsilyl-13β-(4'-chlorobutanoyloxy)milbemycin D
5-O-tert-butyldimethylsilyl-13β-trichloroacryloyloxymilbemycin D
5-O-tert-butyldimethylsilyl-13β-cyclopropanecarbonyloxymilbemycin D
5-O-tert-butyldimethylsilyl-13β-cyclobutanecarbonyloxymilbemycin D
5-O-tert-butyldimethylsilyl-13β-heptanoyloxymilbemycin D
5-O-tert-butyldimethylsilyl-13β-(3'-chloro-2'2'-dimethyl-propionyloxy)milbemycin $A_4$
5-O-tert-butyldimethylsilyl-13β-(3'-chloro-2'2'-dimethyl-propionyloxy)milbemycin D
5-O-tert-butyldimethylsilyl-13β-(1'-methylcyclopropanecarbonyloxy)milbemycin $A_4$
5-O-tert-butyldimethylsilyl-13β-(1'-methylcyclopropanecarbonyloxy)milbemycin D
5-O-tert-butyldimethylsilyl-13β-(1-adamantanecarbonyloxy)milbemycin D
5-O-tert-butyldimethylsilyl-13β-(p-fluorophenoxyacetoxy)milbemycin $A_4$
5-O-tert-butyldimethylsilyl-13β-(2'-chloro-2'-methylpropionyloxy)milbemycin $A_4$
5-O-tert-butyldimethylsilyl-13β-(2',2'-dichloropropionyloxy)milbemycin $A_4$
5-O-tert-butyldimethylsilyl-13β-(2',2'-dimethylbutanoyloxy)milbemycin $A_4$
5-O-tert-butyldimethylsilyl-13β-(3',3'-dimethylbutanoyloxy)milbemycin $A_4$
5-O-tert-butyldimethylsilyl-13β-(2',2',3',3'-tetramethylbutanoyloxy)milbemycin $A_4$
5-O-tert-butyldimethylsilyl-13β-(p-chlorobenzoyloxy)milbemycin $A_4$
5-O-tert-butyldimethylsilyl-13β-(3',3',3'-trifluoropropionyloxy)milbemycin $A_4$
5-O-tert-butyldimethylsilyl-13β-chloroacetoxymilbemycin $A_4$
5-O-tert-butyldimethylsilyl-13β-(2'-chloro-3',3',3'-trifluoropropionyloxy)milbemycin D
5-O-tert-butyldimethylsilyl-13β-(3',3',3'-trifluoropropionyloxy)milbemycin D.

Particularly interesting compounds of formula I are those wherein R is tert-butyl and $R_1$ and $R_2$ are as defined for formula I, and of these in particular those compounds wherein $R_1$ is hydrogen and $R_2$ is ethyl or isopropyl.

The present invention also relates to processes which make it possible to introduce selectively a β-acyloxy group into the 13-position of milbemycin or 13-deoxy-22,23-dihydroavermectinaglycon derivatives and so to obtain highly effective novel parasiticides and insecticides of formula I which may also be used for the formation of further derivatives.

The preparation of esters of formula I, wherein RCOO— is in the β-position, comprises starting from a compound of formula II (II)

[Chemical structure diagram showing a complex polycyclic molecule with labeled positions including 5, 8, 12, 16, 17, with groups CH₃, OH, OR₁, H₃C, A, O, and R₂]

wherein A is one of the groups a or b (a) [= 13β-hydroxy-Δ¹⁴,¹⁵]

(b) [= Δ¹³,¹⁴-15-hydroxy]

and wherein $R_1$ and $R_2$ are as defined for formula I. A compound of formula II, wherein $R_1$ is a protecting group and $R_2$ is as defined for formula I, is treated with a reagent suitable for the introduction of a 13β-ester group. If a free hydroxy compound is desired, the protecting group $R_1$ can subsequently be removed by hydrolysis.

Throughout this specification, compounds of formula II wherein A is the group a shall be referred to as compounds of formula IIa and those compounds of formula II containing the group b shall be referred to as compounds of formula IIb.

Examples of reagents suitable for the introduction of the 13β-ester group into compounds of formula II are:
(a) acids of formula III $$RCOOH \qquad (III)$$

(b) acid amides of formula IV $$RCON(alkyl)_2 \qquad (IV)$$

wherein the alkyl moieties contain 1 to 4 carbon atoms and are preferably methyl,
(c) acid halides of formula V $$RCOhal \qquad (V)$$

wherein hal is halogen, preferably chlorine or bromine,
(d) acid anhydrides of formula VI $$(RCO)_2O \qquad (VI)$$

The acids and acid amides are suitable for all compounds of formula II, but are preferably used for compounds of formula IIb. The acid halides and acid anhydrides are used with compounds of formula IIa.

R in the above formulae III to VI is as defined for formula I.

The reaction for the preparation of compounds of formula I are preferably carried out with compounds of formula IIa or IIb in which the reactive 5-hydroxy group is protected.

Compounds of formula I wherein $R_1$ is a protecting group can be converted by simple, e.g. hydrolytic, removal of the protective function into the highly active free 5-hydroxy derivatives ($R_1=H$) and therefore act as intermediates. However, the biological value of these compounds is not diminished by the protecting group.

The process is generally carried out in an inert solvent or in one of the reactants provided these are liquid. Examples of suitable solvents are: ethers and ethereal compounds such as dialkyl ethers (diethyl ether, diisopropyl ether, tert-butyl methyl ether, dimethoxyethane, dioxane, tetrahydrofuran or anisole); halogenated hydrocarbons such as chlorobenzene, methylene chloride, ethylene chloride, chloroform, carbon tetrachloride or tetrachloroethylene; or sulfoxides such as dimethyl sulfoxide; as well as aromatic or aliphatic hydrocarbons such as benzene, toluene, xylenes, petroleum ether, ligroin or cyclohexane. In some cases it may be of advantage if the reactions are carried out in an inert gas atmosphere (e.g. argon, helium or nitrogen) and/or in absolute solvents. If desired, the final products may be purified in conventional manner, e.g. by washing, digesting, extraction, recrystallisation or chromatography.

The reaction of compounds of formula IIa or IIb with acids of formula III or acid amides of formula IV is carried out in the presence of orthoesters and in the presence of catalytic amounts of a further acid. Acids suitable for the catalysis of the reaction are protonic acids or Lewis acids. Examples of such acids are inorganic acids, e.g. hydrohalic acids such as hydrochloric acid, hydrobromic acid or hydriodic acid, perchloric acid and sulfuric acid, and organic acids such as acetic acid, trifluoroacetic acid, trichloroacetic acid, propionic acid, oxalic acid, formic acid, benzenesulfonic acid, p-toluenesulfonic acid or methanesulfonic acid, as well as Lewis acids such as $BF_3$, $AlCl_3$ or $ZnCl_2$. Particularly preferred acids are p-toluenesulfonic acid (also referred to as TsOH) and sulfuric acid.

The orthoesters required for this reaction are of formula VII $$R_3C(OR_4)_3 \qquad (VII)$$

wherein $R_3$ is hydrogen or $C_1$–$C_4$alkyl, preferably methyl, and $R_4$ is $C_1$–$C_4$alkyl, preferably methyl or ethyl.

When using acids of formula III or acid amides of formula IV for the preparation of compounds of formula I, the reaction temperatures are generally in the range from 0° to 150° C., preferably from 20° to 130° C.

The reaction of compounds of formula IIa with acid halides of formula V or acid anhydrides of formula VI is normally carried out in the above inert solvents in general in the temperature range from −20° to 100° C., preferably from 0° to 70° C. In order to neutralise the acids which form as by-products during the reaction, it is convenient to carry out the reaction in the presence of a neutralising agent.

Suitable neutralising agents are organic bases, e.g. tertiary amines such as trialkylamines (trimethylamine, triethylamine, diisopropylmethylamine or tripropylamine), pyridine and pyridine bases (4-dimethylaminopyridine or 4-pyrrolidylaminopyridine), with pyridine being preferred. The neutralising agent is usually employed in at least equimolar amount, based on the starting materials.

During the reaction of compounds of formula IIb with acids of formula III or acid amides of formula IV in the presence of orthoesters of formula VII and a catalytically effective acid, in addition to the compounds of formula I, compounds of formula VIII

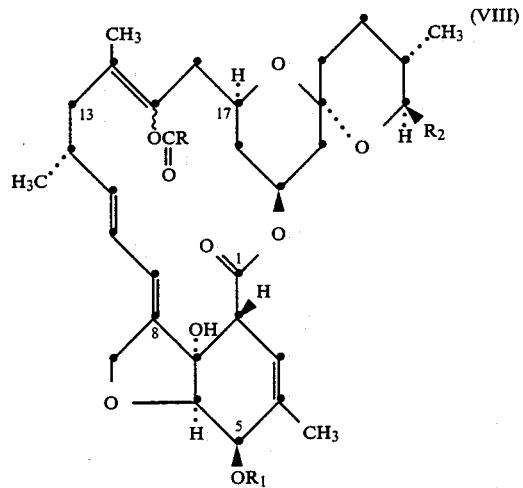

wherein $R_1$, $R_2$ and R are as defined for formula I, may also be formed as by-products.

The reaction products so obtained can be separated by conventional separation methods, e.g. by fractional crystallisation or by chromatography. Chromatography is understood as meaning column, thick-layer or thin-layer chromatography as well as, preferably, high-pressure liquid chromatography over mineral carriers such as silica gel or over organic exchange resins.

In another process variant, the acids of formula III are employed by themselves and the reaction is caried out in the presence of dehydrating reagents. The reaction is carried out for example in the presence of dicyclohexylcarbodiimide and pyridine or in the presence of dialkyl azodicarboxylate and triphenylphosphine.

The starting materials of formula IIa required for preparing compounds of formula I of the present invention by the processes described herein are obtained by reacting compounds of formula IIb with chromate, halochromate or dichromate ions, in particular with pyridinium dichromate [=(Pyr)$_2^+$Cr$_2$O$_7$] or with pyridinium chlorochromate [=(Pyr)$^+$ClCrO$_3$].

Inert anhydrous, preferably polar, solvents are used, e.g. dimethylformamide (=DMF). The reaction is carried out in the temperature range from $-10°$ C. to $+60°$ C., preferably from $+10°$ C. to $+40°$ C.

The compounds of formula IIb [=$\Delta^{13,14}$-15-hydroxy] can be prepared by reacting 14,15-epoxymilbemycins of formula IX

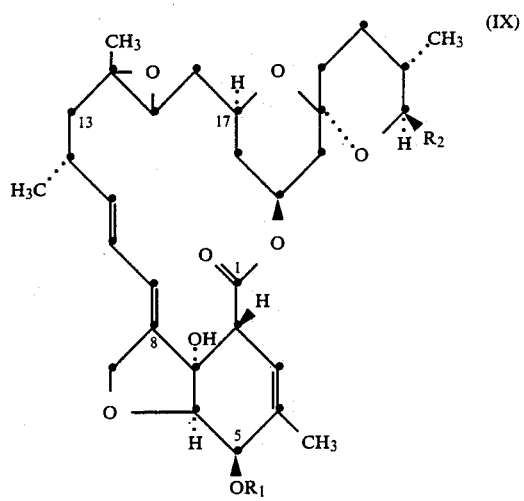

wherein $R_1$ and $R_2$ are as defined for formula I, with the complex reagent [HN$_3$]$_m$/Al(ethyl)$_3$]$_n$, wherein m and n are each independently 1 or 2 or a value between 1 and 2, in an inert dry solvent and in the temperature range from $-30°$ to $+10°$ C., preferably from $-20°$ to $-5°$ C.

Preferred inert solvents are aliphatic and aromatic hydrocarbons such as benzene, toluene, xylene, and petroleum ether; ethers such as diethyl ether, tert-butyl methyl ether, tetrahydrofuran, dioxane, and anisole.

The reaction is conveniently carried out in an inert gas such as nitrogen or argon.

Hydrazoic acid (HN$_3$) can be converted, in the nascent state, into the [HN$_3$]$_m$/[Al(Et)$_3$]$_n$ complex by suspending sodium azide in the stipulated dry solvent or mixture of solvents and generating HN$_3$ in the solution with a stronger acid, e.g. H$_2$SO$_4$ (preferably oleum in order to ensure absolutely dry reaction conditions). Al(Et)$_3$ should already be present in the solution or added thereto shortly afterwards. The epoxy compound to be reacted can also already be present in the solution or added thereto at a suitable time.

The starting compounds of formula IX, which are employed for the preparation of compounds of formula IIb, can be easily prepared by epoxidation of the compounds known from U.S. Pat. No. 3,950,360 and originally designated as "Antibiotics B-41-A", later called "milbemycin A" compounds, and of the compounds known from U.S. Pat. No. 4,346,171 and designated as "B-41-D" or "milbemycin D"; as well as from the 13-deoxy-22,23-dihydroavermectins (R$_2$=sec-butyl) of the formula

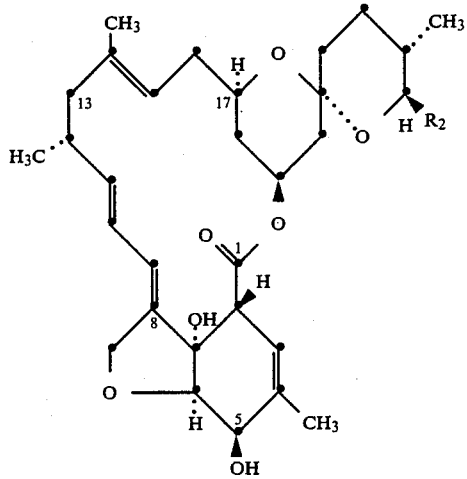

$R_2=CH_3$: milbemycin $A_3$
$R_2=C_2H_5$: milbemycin $A_4$
$R_2=isoC_3H_7$: milbemycin D
$R_2=sec-C_4H_9$: 13-deoxy-22,23-dihydro-C-076-Bla-aglycon, known from U.S. Pat. No. 4,173,571 and from Tetrahedron Letters, Vol. 24, No. 48, pp. 5333–5336 (1983).

The epoxidation is carried out in a solvent phase in the temperature range from $-10°$ to $+20°$ C., preferably from $-5°$ to $+5°$ C.

Peracids such as peracetic acid, trifluoroperacetic acid, perbenzoic acid or chloroperbenzoic acid are suitable for the epoxidation.

The 13β-hydroxy-$\Delta^{14,15}$ compounds of formula IIa can be prepared by reacting compounds of formula IIb, wherein $R_1$ is a protecting group, with pyridinium dichromate $[=(Pyr)_2{}^+Cr_2O_7]$. This reaction is carried out in dimethylformamide and in the temperature range from about $-10°$ to $+60°$ C. If desired, the $R_1$ protecting group is subsequently removed by hydrolysis.

By acylating or silylating the 5-OH group, all those derivatives of formulae I, IIa, IIb and IX are prepared wherein $R_1$ has a meaning other than hydrogen ($R_1$=OH protecting group). The introduction of the acyl group is usually effected with the corresponding acyl halides or acyl anhydrides and is preferably employed to introduce the $R_5C(O)$-group mentioned above. For the silylation it is convenient to use a silane of the formula Y—$Si(R_6)(R_7)(R_8)$, wherein each of $R_6$, $R_7$ and $R_8$ is one of the radicals indicated above. The term acyl halide denotes acyl chloride or acyl bromide and Y is a silyl leaving group. Examples of silyl leaving groups Y are bromide, chloride, cyanide, azide, acetamide, trifluoroacetate or trifluoromethanesulfonate. This recitation constitutes no limitation; further typical silyl leaving groups are known to the skilled person.

5-O-Acylations and 5-O-silylations are carried out in anhydrous medium, preferably in inert solvents and, most preferably, in aprotic solvents. The reaction conveniently takes place in the temperature range from 0° to 80° C., preferably from $+10°$ to $+40°$ C. It is preferred to add an organic base. Examples of suitable bases are tertiary amines such as triethylamine, triethylenediamine, triazole and, preferably, pyridine, imidazole or 1,8-diazabicyclo[5.4.0]-undec-7-ene (DBU).

The removal of these silyl and acyl radicals in the 5-position is effected by selective mild hydrolysis ($\rightarrow R_1$=H) for example with arylsulfonic acid in alcoholic solution or by another method known to the skilled person.

The described process for the preparation of compounds of formula I constitutes in all its partial steps an object of the present invention.

The compounds of formula I are most suitable for controlling pests of animals and plants, including in particular ectoparasites of animals. These last mentioned pests comprise those of the order Acarina, in particular pests of the families Ixodidae, Dermanyssidae, Sarcoptidae, Psoroptidae; of the orders Mallophaga, Siphonaptera, Anoplura (e.g. family of the Haematopinidae); and of the order Diptera, in particular pests of the families Muscidae, Calliphoridae, Oestridae, Tabanidae, Hippoboscidae, and Gastrophilidae.

The compounds of formula I can also be used against hygiene pests, especially of the order Diptera (families Sarcophagidae, Anophilidae and Culicidae); of the order Orthoptera, of the order Dictyoptera (e.g. family of the Blattidae), and of the order Hymenoptera (e.g. family of the Formicidae).

The compounds of formula I also have a lasting action against mites and insects which are parasites of plants. When used to control spider mites of the order Acarina, they are effective against eggs, nymphs and adults of Tetranychidae (Tetranychus spp. and Panonychus spp.) They also have excellent activity against sucking insects of the order Homoptera, in particular against pests of the families Aphididae, Delphacidae, Cicadellidae, Psyllidae, Coccidae, Diaspididae and Eriophyidae (e.g. the rust mite on citrus fruit); of the orders Hemiptera, Heteroptera and Thysanoptera; and against plant-feeding insects of the orders Lepidoptera, Coleoptera, Diptera and Orthoptera.

The compounds of formula I are also suitable for use against soil pests.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radopholus, Rhizoglyphus and others.

Furthermore, the compounds of formula I act against helminths, among which the endoparasitic nematodes can be the cause of severe diseases in mammals and fowl, for example in sheep, pigs, goats, cattle, horses, donkeys, dogs, cats, guinea pigs, cage-birds. Typical nematodes having this indication are: Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. The particular advantage of the compounds of formula I is their activity against those parasites which are resistant to benzimidazole-based parasiticides.

Certain species of the genera Nematodirus, Cooperia and Oesophagostomum attack the intestinal tract of the host animal, whereas others of the species Haemonchus and Ostertagia parasiticise in the stomach and those of the species Dictyocaulus in the lung tissue. Parasites of the families Filariidae and Setariidae are found in internal cell tissue and internal organs, e.g. in the heart, blood vessels, lymph vessels and in subcutaneous tissue. In this connection, particular mention is to be made of the dog heartworm, Dirofilaria immitis. The compounds of formula I are highly effective against these parasites.

The compounds of formula I are also suitable for controlling pathogenic parasites in humans, among which parasites there may be mentioned as typical representatives occurring in the alimentary tract those of the species Ancylostoma, Necator, Ascaris, Strongyloides, Trichinella, Capillaria, Trichuris and Enterobius. The compounds of this invention are also effective against parasites of the species Wuchereria, Brugia, Onchocerca and Loa of the family of the Filariidae which occur in the blood, in tissue and various organs, and, in addition, against Dracunculus and parasites of the species Strongyloides and Trichinella which infest in particular the gastro-intestinal tract.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals at rates of application of 0.01 to 10 mg/kg of body weight. They are applied to enclosed crop areas in amounts of 10 g to 1000 g per hectare. They are also used in pens, livestock buildings or other buildings.

The formulations, i.e. the compositions, preparations or mixtures containing the compound of formula I (active ingredient) are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the active ingredient to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide or phospholipides.

The surfactants customarily employed in the art of formulation are described e.g. in "McCutcheon's Detergents and Emulsifiers Annual", MC Publishing Corp. Ridgewood, N.J., 1982.

The pesticidal compositions usually contain 0.01 to 95%, preferably 0.1 to 80%, of a compound of formula I, 5 to 99.99% of a solid or liquid adjuvant, and 0 to 25%, preferably 0.1 to 25%, of a surfactant.

Whereas commercial products are preferably formulated as concentrates, the end user will normally employ dilute formulations having a concentration of 1–10,000 ppm.

The invention therefore also relates to pesticidal compositions which contain as active ingredient at least one compound of formula I, together with customary carriers and/or dispering agents.

The compositions may also contain further ingredients, such as stabilisers, antifoams, viscosity regulators, binders, tackifiers as well as fertilisers or other active ingredients for obtaining special effects.

PREPARATORY EXAMPLES

1. Preparation of starting materials and intermediates

EXAMPLE 1.1

Preparation of 14,15-epoxymilbemycin D (formula IX)

While cooling with ice, a solution of 170 mg of chloroperbenzoic acid in 5 ml of dichloromethane is added to a solution of 550 mg of milbemycin D in 5 ml of dichloromethane. After stirring for 1 hour at 0° to +5° C., another 170 mg of the oxidising agent are added and stirring is continued for 30 minutes. When the reaction is complete, the solution is poured into an ice-cooled solution of sodium sulfite and extracted with ethyl acetate. The combined extracts are washed once with water, dried, and concentrated by evaporation in vacuo. The crude product is purified by chromatography through a column of silica gel (elution with a 20:15 mixture of n-hexane and ethyl acetate), affording 450 mg of amorphous, white 14,15-epoxymilbemycin D.

EXAMPLE 1.2

Preparation of 15-hydroxy-$\Delta^{13,14}$-milbemycin D (formula IIb)

9.5 ml (0.41 g; 9.53 mmol) of a 6.96% solution of $HN_3$ in diethyl ether are added at −20° C. to a solution of 2.1 ml (1.75 g; 15.3 mmol) of triethyl aluminium in 8.5 ml of absolute diethyl ether. The reaction mixture is then added at −10° C. to 1.8 g (3.15 mmol) of 14,15-epoxymilbemycin D (in substance). The ensuing reaction is strongly exothermic. After 1 hour at room temperature, 4 ml of absolute ether are added and the gelatinous reaction mixture is vigorously stirred. After 4 hours the reaction mixture is worked up as described in Example 1.1. Chromatographic purification through 70 g of silica gel (elution with a 10:1 mixture of $CH_2Cl_2$ and acetone) affords 200 mg (10%) of 14-azido-15-hydroxymilbemycin D and 820 mg (45%) of 15-hydroxy-$\Delta^{13,14}$-milbemycin D; m.p. 151°–153° C. (recrystallisation from methanol).

EXAMPLE 1.3

Preparation of 5-O-tert-butyldimethylsilyl-14,15-epoxymilbemycin D (formula IX)

A solution of 2.21 g (3.86 mmol) of 14,15-epoxymilbemycin D, 757 mg (5.02 mmol) of tert-butyldimethylchlorosilane and 342 mg (5.02 mmol) of imidazole in 4 ml of dimethylformamide is stirred for 90 minutes at room temperature. Then 80 ml of diethyl ether are added and the mixture is filtered through 20 g of silica gel and the filtrate is concentrated, affording 2.65 g (100%) of 5-O-tert-butyldimethylsilyl-14,15-epoxymilbemycin D.

$^1$H-NMR (300 MHz., solvent $CDCl_3$., δ values based on $Si(CH_3)_4$ (=tetramethylsilane=TMS)): 0.12 ppm (s) $(CH_3)_2Si-O-$; 0.92 ppm (s) $(t-C_4H_9)Si-O-$; 1.23 ppm (broad s) ($C_{14}CH_3$, i.e. signal of the $CH_3$ group in the 14-position); 2.56 ppm (d; J=9 Hz) ($C_{15}H$, i.e. signal of the proton in the 15-position).

Following the same procedure, the corresponding 5-O-trimethylsilyl-14,15-epoxymilbemycin D (m.p. 92°–97° C.) can be prepared by reaction with trimethylsilyl trifluoromethanesulfonate.

EXAMPLE 1.4

Preparation of 5-O-tert-butyldimethylsilyl-15-hydroxy-$\Delta^{13,14}$-milbemycin D (formula IIb)

A solution of the $HN_3/Et_3Al$ complex reagent (prepared from a solution of 4.97 ml of triethyl aluminium in 7 ml of absolute tetrahydrofuran and 9.15 ml of a 2.39 molar solution of $HN_3$ (21.9 mmol) in absolute diethyl ether) is added, under argon, to a solution of 5.0 g (7.29 mmol) of 5-O-tert-butyldimethylsilyl-14,15-epoxymilbemycin D in about 20 ml of absolute tetrahydrofuran, and the mixture is heated under reflux for 15 hours. Then 250 ml of ether, 2 ml of methanol, and finally a mixture of 10 g of $Na_2SO_4.10H_2O$ and 10 g of celite are added at room temperature. The mixture is filtered and the filtrate is concentrated and chromatographic purification of the crude product through 160 g silica gel (elution with 0–30% of ethyl acetate in hexane) affords 2.37 g (47%) of 5-O-tert-butyldimethylsilyl-15-hydroxy-$\Delta^{13,14}$-milbemycin D.

$^1$H-NMR (300 MHZ, $CDCl_3$): 1.59 ppm (d; J=1 Hz) ($C_{14}CH_3$); 4.06 ppm (dd; $J_1$=11 Hz; $J_2$=4 Hz) ($C_{15}H$); 5.15 ppm (d; J=8 Hz) ($C_{13}H$).

In addition, 109 mg (2%) of 13β-azido-5-O-tert-butyldimethylsilylmilbemycin D are obtained.

EXAMPLE 1.5

Preparation of 14,15-epoxymilbemycin $A_4$ ($R_2$=$C_2H_5$) (formula IX)

A solution of 2.43 g (14.08 mmol) of m-chloroperbenzoic acid in 70 ml of dichloromethane is added dropwise at room temperature to a solution of 5.7 g (10.5 mmol) of milbemycin $A_4$ in 140 ml of dichloromethane and 120 ml of a 0.5 molar solution of $NaHCO_3$. The mixture is vigorously stirred for 1 hour at room temperature and then diluted with 300 ml of dichloromethane. The organic phase is washed with an aqueous solution of $NaHCO_3$, dried over $Na_2SO_4$ and concentrated, affording 5.7 g of epoxide as crude product.

EXAMPLE 1.6

Preparation of 5-O-tert-butyldimethylsilyl-14,15-epoxymilbemycin $A_4$ (formula IX)

5.7 g of 14,15-epoxy-milbemycin $A_4$ are dissolved in 10 ml of dry dimethylformamide. Then 0.63 g (9.16 mmol) of imidazole and 1.4 g (9.34 mmol) of tert-butyldimethylchlorosilane are added at room temperature. The mixture is stirred for 1 hour at room temperature and chromatographed through 150 g of silica gel (elution with a 4:1 mixture of hexane and ether), affording 2.84 g (40% of theory, based on milbemycin $A_4$) of the silylated epoxy derivative.

EXAMPLE 1.7

Preparation of 5-O-tert-butyldimethylsilyl-15-hydroxy-$\Delta^{13,14}$-milbemycin $A_4$ (formula IIb)

The complex reagent $HN_3/Al(ethyl)_3$ is prepared as follows: To 2.8 ml (12.2 mmol) of $Al(C_2H_5)_3$ in 4 ml of absolute tetrahydrofuran are slowly added at about −20° C., under argon, 5.28 ml (20.4 mmol) of a 10% solution of $HN_3$ in absolute diethyl ether. To this solution is added, under argon, a solution of 2.84 g (4.25 mmol) of 5-O-tert-butyldimethylsilyl-14,15-epoxymilbemycin $A_4$ (Ex. 1.6) in about 12 ml of absolute tetrahydrofuran, and the mixture so obtained is heated for 4 hours under reflux. Then 500 ml of diethyl ether and 10 g of $Na_2SO_4.10H_2O$ and 10 g of celite are added at room temperature. The mixture is filtered and the filtrate is concentrated. Chromatography of the crude product through 100 g of silica gel (elution with a 7:2 mixture of hexane and diethyl ether) affords 1.72 g (60% of theory) of the title compound.

$^1$H-NMR (300 MHz, $CDCl_3$): 1.59 ppm (broad s) ($C_{14}CH_3$); 4.05 ppm (broad s) ($C_{15}H$); 5.15 ppm (d; J=6

Hz) (C$_{13}$H). In addition, 0.1 g of 13β-azido-5-O-tert-butyldimethylsilylmilbemycin A$_4$ is obtained.

EXAMPLE 1.8

Preparation of 15-hydroxy-Δ$^{13,14}$-milbemycin A$_4$ (formula IIb)

Hydrolysis of 5-O-tertbutyldimethylsilyl-b 15-hydroxy-Δ$^{13,14}$-milbemycin A$_4$ (Ex. 1.7) with a 1% solution of p-toluenesulfonic acid in methanol and working up in diethyl ether with a 5% aqueous solution of sodium bicarbonate affords the title compound.

EXAMPLE 1.9

Preparation of 14,15-epoxymilbemycin A$_3$ (R$_2$=CH$_3$) (formula IX)

In accordance with the procedure described in Example 1.1, reaction of 220 mg of milbemycin A$_3$ in 5 ml of dichloromethane and 320 mg of benzoperacid in 5 ml of dichloromethane at −2° to +5° C. over 1½ hours and purification through a column of silica gel affords 190 mg of 14,15-epoxymilbemycin A$_3$.

EXAMPLE 1.10

Preparation of 5-O-t-butyldimethylsilyl-14,15-epoxymilbemycin A$_3$ (formula IX)

In accordance with the procedure of Example 1.3, reaction of 190 mg of 14,15-epoxymilbemycin A$_3$ and 120 mg of tert-butyldimethylchlorosilane in the presence of imidazole affords 217 mg of the title compound.

EXAMPLE 1.11

Preparation of 5-O-tert-butyldimethylsilyl-15-hydroxy-Δ$^{13,14}$-milbemycin A$_3$ (formula IIb)

In accordance with the epoxy cleavage of Example 1.2, 203 mg of the title compound are obtained from 210 mg of 5-O-tert-butyldimethylsilyl-14,15-epoxymilbemycin A$_3$ in absolute diethyl ether using the complex reagent HN$_3$/Et$_3$Al under argon, and subsequent purification.

$^1$H-NMR (300 MHz, CDCl$_3$): 1.58 ppm (broad s) (C$_{14}$CH$_3$); 4.05 ppm (broad s) (C$_{15}$H); 5.15 ppm (d; J=6 Hz) (C$_{13}$H).

EXAMPLE 1.12

Preparation of 15-hydroxy-Δ$^{13,14}$-milbemycin A$_3$ (formula IIb)

In accordance with the procedure described in Example 1.4, the reagent HN$_3$/Al(C$_2$H$_5$)$_3$ is freshly prepared and added dropwise at −10° C. to a solution of 830 mg (3.05 mmol) of 14,15-epoxymilbemycin A$_3$ in 7 ml of dry diethyl ether. After working up, 385 mg of 15-hydroxy-Δ$^{13,14}$-milbemycin A$_3$ and 92 mg of 14-azido-15-hydroxymilbemycin A$_3$ are obtained.

EXAMPLE 1.13

Preparation of 13-deoxy-14,15-epoxy-22,23,dihydroavermectin-Bla-aglycon (R$_2$=sec-C$_4$H$_9$) (formula IX)

In accordance with the procedure described in Example 1.1, 510 mg of the title compound are obtained from 520 mg of 13-deoxy-22,23-dihydroavermectin-Bla-aglycon [U.S. Pat. No. 4,173,571 and Tetrahedron Letters, Vol. 24, No. 48, pp. 5333–5336 (1983)] and 210 mg of m-chlorobenzoperacid in 20 ml of dichloromethane.

EXAMPLE 1.14

Preparation of 5-O-tert-butyldimethylsilyl-13-deoxy-14,15-epoxy-22,23-dihydroavermectin-Bla-aglycon (formula IX)

In accordance with the procedure described in Example 1.3, 108 mg of the title compound are obtained from 220 mg of 13-deoxy-14,15-epoxy-22,23-dihydroavermectin-Bla-aglycon (Ex. 1.13) and 55 mg of tert-butyldimethylchlorosilane in the presence of 25 mg of imidazole in 5 ml of dry dimethylformamide.

EXAMPLE 1.15

Preparation of 13-deoxy-15-hydroxy-Δ$^{13,14}$-22,23-dihydroavermectin-Bla-aglycon (formula IIb)

In accordance with the procedure described in Example 1.4, 112 mg of the title compound are obtained by reacting 220 mg of 13-deoxy-14,15-epoxy-22,23-dihydroavermectin-Bla-aglycon (Ex. 1.13) with the complex reagent consisting of 320 mg of Al(C$_2$H$_5$)$_3$ and 110 mg of a 6.96% solution of HN$_3$ in a total of 16 ml of dry diethyl ether. In addition, 61 mg of 13-deoxy-14-azido-15-hydroxy-22,23-dihydroavermectin-Bla-aglycon are obtained.

EXAMPLE 1.16

Preparation of 5-O-tert-butyldimethylsilyl-13β-hydroxymilbemycin D and 13β-hydroxymilbemycin D (formula IIa)

A solution comprising 286 mg (0.41 mmol) of 5-O-tert-butyldimethylsilyl-15-hydroxy-Δ$^{13,14}$-milbemycin D and 209 mg (0.56 mmol) of pyridinium dichromate (PDC) in 3 ml of dimethylformamide (DMF) is stirred for 30 minutes at room temperature. 1 ml of isopropanol is subsequently added and the mixture is stirred for 5 minutes and then diluted with 50 ml of ether. After a further 10 minutes, the mixture is filtered through silical gel and the filtrate is concentrated. Chromatographic purification of the crude product through 20 g of silica gel (elution with a 1:2 mixture of ether and hexane) affords 165 mg (57%) of 5-O-tert-butyldimethylsilyl-13β-hydroxymilbemycin D.

$^1$H-NMR (300 MHz; CDCl$_3$; TMS): 1.59 ppm (br. s) (C$_{14}$CH$_3$) 3.70 ppm (d; J=10 Hz) (C$_{13}$H).

105 mg (0.153 mmol) of the compound so obtained are stirred at room temperature in 1 ml of a 1% solution of p-toluenesulfonic acid in methanol for 1 hour. The mixture is diluted with 20 ml of ether, filtered through silica gel and the filtrate is concentrated. The residue is chromatographed through about 10 g of silica gel (elution with a 1:4 mixture of acetone and dichloromethane), affording 73 mg (83%) of 13β-hydroxymilbemycin D.

$^1$H-NMR (300 MHz; CDCl$_3$; TMS): 1.58 ppm (br. s) (C$_{14}$CH$_3$) 3.17 ppm (d; J=10 Hz) (C$_{13}$H).

EXAMPLE 1.17

Preparation of 5-O-tert-butyldimethylsilyl-13β-hydroxymilbemycin A$_4$

A solution comprising 1.06 g (1.59 mmol) of 5-O-tert-butyldimethylsilyl-15-hydroxy-Δ$^{13,14}$-milbemycin A$_4$ and 383 mg (1.02 mmol) of pyridinium dichromate (PDC) in 5 ml of dimethylformamide (DMF) is stirred for 30 minutes at room temperature. 1 ml of isopropanol is subsequently added and the mixture is stirred for 5 minutes and then diluted with 50 ml of ether. After a further 10 minutes, the mixture is filtered through silica gel and the filtrate is concentrated. Chromatographic purification of the crude product through 20 g of silia gel (elution with a 1:2 mixture of ether and hexane) affords 625 mg (59%) of 5-O-tert-butyldimethylsilyl-13$\beta$-hydroxymilbemycin A$_4$.

$^1$H-NMR (300 MHz; CDCl$_3$; TMS): 0.98 ppm (t; J=7 Hz) (CH$_3$CH$_2$) 1.95 ppm (br. s) (C$_{14}$CH$_3$) 3.69 ppm (d; J=9 Hz) (C$_{13}$H).

2. Preparation of the final products

EXAMPLE 2.1

Preparation of 13$\beta$-pivaloyloxymilbemycin D and 15-pivaloyloxy-$\Delta^{13,14}$-milbemycin D A solution of 278 mg (0.40 mmol) of 5-O-tert-butyldimethylsilyl-15-hydroxy-$\Delta^{13,14}$-milbemycin D, 208 mg (2.04 mmol) of pivalic acid and 129 mg (0.80 mmol) of triethyl orthoacetate in 2 ml of absolute toluene is heated for 5 minutes to 130° C. in a flask equipped with a Claisen stillhead. Working up and chromatographic purification through 100 g of silica gel (elution with a 5:1 mixture of hexane and diethyl ether) affords 200 mg (64%) of 5-O-tert-butyldimethylsilyl-13$\beta$-pivaloyloxymilbemcycin D and 100 mg (32%) of 5-O-tert-butyldimethylsilyl-15-pivaloyloxy-$\Delta^{13,14}$-milbemycin D. Both of these silyl ethers are treated with a solution of 3 ml of 1% p-toluenesulfonic acid (TsOH) in methanol (MeOH) for 2 hours at room temperature, affording 165 mg (96%) of 13$\beta$-pivaloyloxymilbemycin D $^1$H-NMR (300 MHz; CDCl$_3$; TMS): 1.19 ppm (s) ((CH$_3$)$_3$C) 1.56 ppm (br. s) (C$_{14}$CH$_3$) 4.90 ppm (d; J=10.6 Hz) (C$_{13}$H).

and 82 mg (95%) of 15-pivaloyloxy-$\Delta^{13,14}$-milbemycin D.

$^1$H-NMR (300 MHz; CDCl$_3$; TMS): 1.18 ppm (s) ((CH$_3$)$_3$C); 1.53 ppm (br. s) (C$_{14}$CH$_3$); 5.16 ppm (dd; J=9 and 5 Hz) (C$_{15}$H).

In accordance with the procedure described in Example 2.1, the following compounds are prepared by starting from 5-O-tert-butyldimethylsilyl-15-hydroxymilbemycin A$_4$:

2.1.1   13$\beta$-(2',2'-Dimethylbutanoyloxy)milbemycin A$_4$ $^1$H-NMR (300 MHz, CDCl$_3$, TMS): 1.13 ppm (s) (CH$_3$CH$_2$C(CH$_3$)$_2$CO); 4.91 ppm (d, J=10.5 Hz) (C$_{13}$H).

2.1.2   13$\beta$-(3',3'-Dimethylbutanoyloxymilbemycin A$_4$)

$^1$H-NMR (300 MHz, CDCl$_3$, TMS): 1.01 ppm (s) (C(CH$_3$)$_3$CH$_2$CO); 1.58 ppm (br. s) (C$_{14}$CH$_3$); 4.95 ppm (d, J=10.5 Hz) (C$_{13}$H).

2.1.3   13$\beta$-(3'-Chloro-2',2'-dimethylpropionyloxy)-milbemycin A$_4$ $^1$H-NMR (300 MHz, CDCl$_3$, TMS): 1.27, 1.28 ppm (2s) (ClCH$_2$C(CH$_3$)$_2$CO); 1.55 ppm (s) (C$_{14}$CH$_3$); 3.60 ppm (br. s) (ClCH$_2$C(CH$_3$)$_2$CO); 4.94 ppm (d, J=10.5 Hz) (C$_{13}$H).

2.1.4   13$\beta$-(2'-Chloro-2'methylpropionyloxy)milbemycin A$_4$ $^1$H-NMR (300 MHz, CDCl$_3$, TMS): 1.51 ppm (s) (2CH$_3$-CCl-CO); 4.92 ppm (d, J=10 Hz) (C$_{13}$H)

2.1.5   13$\beta$-(2'2'-Dichloropropionyloxy)milbemycin A$_4$ $^1$H-NMR (300 MHz, CDCl$_3$, TMS): 1.53 ppm (s) (CH$_3$-CCl$_2$-CO); 4.94 ppm (d, J=10 Hz) (C$_{13}$H).

EXAMPLE 2.2

Preparation of 13$\beta$-pivaloyloxymilbemycin D 0.4 ml (2.9 mmol) of triethylamine and 0.18 ml (1.45 mmol) of pivaloyl chloride are added to a solution of 200 mg (0.29 mmol) of 5-O-tert-butyldimethylsilyl-13$\beta$-hydroxymilbemycin D in 5 ml of dry chloroform and, under nitrogen, the mixture is heated under reflux for 2 hours. Treatment of the crude product (200 mg) with 3 ml of a 1% solution of p-TsOH in MeOH for 2 hours at room temperature affords 166 mg (86%) of 13$\beta$-pivaloyloxymilbemycin D.

In accordance with the procedure described in Example 2.2, the following compounds are obtained by starting from 5-O-tert-butyldimethylsilyl-13$\beta$-hydroxymilbemycin D or A$_4$ 2.2.1  13$\beta$-(2',2',3',3'-Tetramethylbutanoyloxy)milbemycin A$_4$ $^1$H-NMR (300 MHz, CDCl$_3$, TMS): 0.92 ppm (s) (C(CH$_3$)#3)$_2$CO); 1.13, 1.14 ppm (2s) (C(CH$_3$)$_3$C(CH$_3$)$_2$CO); 1.54 ppm (br. s) (C$_{14}$CH$_3$); 4.96 ppm (d, J=10.5 Hz) (C$_{13}$H).

2.2.2 13$\beta$-(2'-Methoxy-2'-methylpropionyloxy)milbemycin D $^1$H-NMR (300 MHz, CDCl$_3$, TMS): 1.41 ppm (s) (CH$_3$OC(CH$_3$)$_2$CO); 3.25 ppm (s) (CH$_3$OC(CH$_3$)$_2$CO); 4.97 ppm (d, J=10.5 Hz) (C$_{13}$H).

2.2.3 13$\beta$-(2'-Methoxy-2'-methylpropionyloxy)milbemycin A$_4$ $^1$H-NMR (300 MHz, CDCl$_3$, TMS): 1.41 ppm (s) (CH$_3$OC(CH$_3$)$_2$CO); 3.26 ppm (s) (CH$_3$OC(CH$_3$)$_2$CO); 4.97 ppm (d, J=10.5 Hz) (C$_{13}$H).

2.2.4 13$\beta$-Trichloroacetoxymilbemycin D $^1$H-NMR (250 MHz, CDCl$_3$, TMS): 1.62 ppm (s) (C$_{14}$CH$_3$); 4.99 ppm (d, J=10 Hz) (C$_{13}$H).

2.2.5   13$\beta$-(cis/trans-2',2'-Dimethyl-3'-[2'',2''-dichlorovinyl]cyclopropanecarbonyloxy)milbemycin D $^1$H-NMR (300 MHz; CDCl$_3$; TMS): 1.55 ppm (br. s) (C$_{14}$CH$_3$); 1.87 ppm (br. s) (C$_4$CH$_3$); 4.91 ppm (d, J=10.2 Hz) (C$_{13}$H); 4.94 ppm (d, J=10.7 Hz) (C$_{13}$H); 6.20 ppm (d, J=8.8 Hz) (Cl$_2$C=CH); 6.24 ppm (d, J=8.8 Hz) (Cl$_2$C=CH).

EXAMPLE 2.3

Preparation of 13$\beta$-pivaloyloxymilbemycin A$_4$ 0.2 ml (1.5 mmol) of triethylamine and 0.09 ml (0.07 mmol) of pivaloyl chloride are added to a solution of 100 mg (0.15 mmol) of 5-O-tert-butyldimethylsilyl-13$\beta$-hydroxymilbemycin A$_4$ in 2.5 ml of dry chloroform and, under nitrogen, the mixture is then heated under reflux for 2 hours. Treatment of the crude product (100 mg) with 3 ml of a 1% solution of p-TsOH in MeOH for 2 hours at room temperature affords 82 mg (85%) of 13$\beta$-pivaloyloxymilbemycin A$_4$.

$^1$H-NMR (300 MHz; CDCl$_3$; TMS): 1.20 ppm (s) ((CH$_3$)$_3$C); 0.98 ppm (t, J=7 Hz), (CH$_3$CH$_2$); 1.53 ppm (br. s) (C$_{14}$CH$_3$); 4.90 ppm (d; J=10,5 Hz) (C$_{13}$H).

EXAMPLE 2.4

Preparation of 13$\beta$-acetoxymilbemycin D

A solution of 200 mg (0.29 mmol) of 5-O-tert-butyldimethylsilyl-13$\beta$-hydroxymilbemycin D and 1 ml of pyridine in 2 ml of acetic anhydride is stirred for 2 hours at room temperature. Working up in diethyl ether affords 212 mg of crude product which is treated with a 1% solution of p-TsOH in methanol for 1 hour at room temperature. 162 mg (90%) of 13β-acetoxymilbemycin D are obtained.

$^1$H-NMR (300 MHz; CDCl$_3$; TMS): 1.56 ppm (br. s) (C$_{14}$CH$_3$) 1.87 ppm (br. s) (C$_4$CH$_3$) 2.04 (s) (CH$_3$COO) 4.94 ppm (d; J=10.5 Hz) (C$_{13}$H)

EXAMPLE 2.5

Preparation of 5-O-tert-butyldimethylsilyl-15-acetoxy-Δ$^{13,14}$-milbemycin D

A solution of 627 mg (0.914 mmol) of 5-O-tert-butyl-dimethylsilyl-15-hydroxy-Δ$^{13,14}$-milbemycin D in 2 ml of acetic anhydride and 2 ml of pyridine is stirred for ½ hour at room temperature. Working up in diethyl ether with 5% aqueous NaHCO$_3$ solution and 1M HCl and filtration through silica gel affords 624 mg (94%) of 5-O-tert-butyldimethylsilyl-15-acetoxy-Δ$^{13,14}$-milbemycin D.

$^1$H-NMR (300 MHz; CDCl$_3$; TMS): 1.58 ppm (br. s) (C$_{14}$CH$_3$) 1.79 ppm (br. s) (C$_4$CH$_3$) 2.02 ppm (s) (CH$_3$COO) 5.12–5.26 ppm (m) (C$_{10}$H; C$_{13}$H; C$_{15}$H).

EXAMPLE 2.6

Preparation of 13β-formyloxymilbemycin D

A solution of 136 mg (0.198 mmol) of 5-O-tert-butyl-dimethylsilyl-15-hydroxy-Δ$^{13,14}$-milbemycin D and 0.1 ml of triethyl orthoacetate in 3 ml of an H$_2$SO$_4$/diisopropyl ether/dimethylformamide mixture (1:10:90) is stirred for 10 minutes at room temperature. Working up in hexane with 5% aqueous NaHCO$_3$ solution and water and chromatographic purification of the crude product through 20 g of silica gel (elution with a 1:4 mixture of ethyl acetate and hexane) affords 80 mg (57%) of 5-O-tert-butyldimethylsilyl-13β-formyloxymilbemycin D.

Treatment of 155 mg (0.217 mmol) of 5-O-tert-butyl-dimethylsilyl-13β-formyloxymilbemycin D with 2 ml of a 40% aqueous solution of HF and acetonitrile (1:99) for 2 hours at room temperature followed by working up in diethyl ether with 5% aqueous NaHCO$_3$ solution and chromatographic purification through 20 g of silica gel (elution with a 2:3 mixture of ethyl acetate and hexane) affords 105 mg (81%) of 13β-formyloxymilbemycin D.

$^1$H-NMR (300 MHz; CDCl$_3$; TMS): 1.56 ppm (br. s) (C$_{14}$CH$_3$); 1.87 ppm (br. s) (C$_4$CH$_3$); 5.05 ppm (d, J=10.5 Hz) (C$_{13}$H); 8.08 ppm (s) (OCHO).

mass spectrum m/e: 600 (M$^+$, C$_{34}$H$_{48}$O$_9$), 472, 426, 293, 209, 181, 151.

EXAMPLE 2.7

Preparation of 13β-pivaloyloxymilbemycin A$_4$

A solution of 100 mg (0.149 mmol) of 5-O-tert-butyl-dimethylsilyl-15-hydroxy-Δ$^{13,14}$-milbemycin A$_4$, 100 mg (1.02 mmol) of pivalic acid and 65 mg (0.40 mmol) of triethyl orthoacetate in 2 ml of absolute toluene is heated for 5 minutes to 130° C. in a flask equipped with a Claissen stillhead. Working up and chromatographic purification through 100 g of silica gel (elution with a 5:1 mixture of hexane and diethyl ether) affords 73 mg (65%) of 5-O-tert-butyldimethylsilyl-13β-pivaloyloxymilbemycin A$_4$. The silyl ether is treated with a solution of 3 ml of 1% toluenesulfonic acid in methanol for 2 hours at room temperature, affording 60 mg (96%) of 13β-pivaloyloxymilbemycin A$_4$.

EXAMPLE 2.8

Preparation of 13β-heptanoyloxymilbemycin D

At 0° C., 31 mg (0.21 mmol) of heptanoyl chloride in 0.5 ml of dichloromethane are cautiously added to a solution of 120 mg (0.175 mmol) of 5-O-tert-butyldimethylsilyl-13β-hydroxymilbemycin D in 2 ml of pyridine. The mixture is then worked up, and treatment of the crude product with 3 ml of a solution of 1% p-TsOH in MeOH for 2 hours at room temperature affords 115 mg (96%) of 13β-heptanoyloxymilbemycin D.

$^1$H-NMR (300 MHz; CDCl$_3$; TMS): 1.53 ppm (br. s) (C$_{14}$CH$_3$); 1.87 ppm (br. s) (C$_4$CH$_3$); 4.95 ppm (d, J=10.5 Hz) (C$_{13}$H).

EXAMPLE 2.9

Preparation of 13β-(4'-chlorobutanoyloxy)milbemycin D

At 0° C., 24.5 mg (0.174 mmol) of 4-chlorobutyryl chloride in 0.5 ml of dichloromethane are cautiously added to a solution of 100 mg (0.145 mmol) of 5-O-tert-butyldimethylsilyl-13β-hydroxymilbemycin D in 1 ml of pyridine and 2 ml of dichloromethane. The mixture is then worked up, and treatment of the crude product with 3 ml of a solution of 1% p-TsOH in MeOH for 2 hours at room temperature affords 92.6 mg (94%) of 13β-(4'-chlorobutanoyloxy)milbemycin D.

$^1$H-NMR (300 MHz; CDCl$_3$; TMS): 1.54 ppm (br. s) (C$_{14}$CH$_3$) 1.82 ppm (br. s) (C$_4$CH$_3$) 3.58 ppm (d, J=6,3 Hz) (2H-C$_4$') 4.96 ppm (d, J=10.5 Hz) (C$_{13}$H).

EXAMPLE 2.10

Preparation of 13β-(3'chloro-2',2'-dimethylpropionyl)milbemycin D

A solution of 100 mg (0.145 mmol) of 5-O-tert-butyl-dimethylsilyl-15-hydroxy-Δ$^{13,14}$-milbemycin D, 78 mg (0.57 mmol) of 3-chloro-2,2-dimethylpropionic acid and 47 mg (0.29 mmol) of triethyl orthoacetate in 3 ml of absolute toluene is heated for 5 minutes to 100° C. in a flask equipped with a Claisen stillhead. Working up and chromatographic purification through 60 g of silica gel (elution with a 5:1 mixture of hexane and diethyl ether) affords 50 mg of 5-O-tert-butyldimethylsilyl-13β-(3'chloro-2',2'-dimethylpropionyloxy)milbemycin D. The silyl ether is treated with a solution of 3 ml of 1% TsOH in MeOH for 2 hours at room temperature, affording 41 mg (41%) of 13β-(3'-chloro-2'2'-dimethylpropionyloxy)milbemycin D.

$^1$H-NMR (300 MHz; CDCl$_3$; TMS): 1.27 ppm (s, 2CH$_3$-C$_2$'); 1.54 ppm (br. s) (C$_{14}$CH$_3$); 1.87 ppm (br. s) (C$_4$CH$_3$); 4.96 ppm (d, J=10.5 Hz) (C$_{13}$H).

EXAMPLE 2.11

Preparation of 13β-cyclopropanecarbonyloxymilbemycin D

A solution of 150 mg (0.125 mmol) of 5-O-tert-butyl-dimethylsilyl-15-hydroxy-Δ$^{13,14}$-milbemycin D, 94 mg (1.075 mmol) of cyclopropanecarboxylic acid and 71 mg (0.47 mmol) of triethyl orthoacetate in 2 ml of absolute toluene is heated for 5 minutes to 100° C. in a flask equipped with a Claisen stillhead. Working up and chromatographic purification through 80 g of silica gel (elution with a 5:1 mixture of hexane and diethyl ether) affords 100 mg of 5-O-tert-butyldimethylsilyl-13β- cyclopropanecarbonyloxymilbemycin D. The silyl ether is treated with a solution of 3 ml of 1% TsOH in MeOH for 2 hours at room temperature, affording 75 mg (53%) of 13β-cyclopropanecarbonyloxymilbemycin D.

$^1$H-NMR (300 MHz; CDCl$_3$; TMS): 1.55 ppm (br. s) (C$_{14}$CH$_3$); 1.87 ppm (br. s) (C$_4$CH$_3$); 4.95 ppm (d, J=10.5 Hz) (C$_{13}$H).

EXAMPLE 2.12

Preparation of 13β-(1'-methylcyclopropanecarbonyloxy)milbemycin D

A solution of 278 mg (0.40 mmol) of 5-O-tert-butyldimethylsilyl-15-hydroxy-Δ$^{13,14}$-milbemycin D, 204 mg (2.04 mmol) of 1-methylcyclopropanecarboxylic acid and 132 mg (0.82 mmol) of triethyl orthoacetate in 5 ml of absolute toluene is heated for 5 minutes to 100° C. in a flask equipped with a Claisen stillhead. Working up and chromatographic purifiction through 100 g of silica gel (elution with a 5:1 mixture of hexane and diethyl ether) affords 150 mg of 5-O-tert-butyldimethylsilyl-13β-(1'-methylcyclopropanecarbonyloxy)milbemycin D. The silyl ether is treated with a solution of 3 ml of 1% TsOH in MeOH for 2 hours at room temperature, affording 127 mg (48%) of 13β-(1'-methylcyclopropanecarbonyloxy)milbemycin D.

$^1$H-NMR (300 MHz; CDCl$_3$; TMS): 1.28 ppm (s) (C$_1$'CH$_3$); 1.52 ppm (br.s) (C$_{14}$CH$_3$); 1.87 ppm (br. s) (C$_4$CH$_3$); 4.91 ppm (d, J=10.5 Hz) (C$_{13}$H).

EXAMPLE 2.13

Preparation of 13β-(1'-methylcyclopropanecarbonyloxy)milbemycin A$_4$

A solution of 140 mg (0.206 mmol) of 5-O-tert-butyldimethylsilyl-15-hydroxy-Δ$^{13,14}$-milbemycin A$_4$, 102 mg (1.01 mmol) of 1-methylcyclopropanecarboxylic acid and 66 mg (0.41 mmol) of triethyl orthoacetate in 5 ml of absolute toluene is heated for 5 minutes to 100° C. in a flask equipped with a Claisen stillhead. Working up and chromatographic purification through 40 g of silica gel (elution with a 5:1 mixture of hexane and diethyl ether) affords 58 mg of 5-O-tert-butyldimethylsilyl-13β-(1'-methylcyclopropanecarbonyloxy)milbemycin A$_4$. The silyl ether is treated with a solution of 3 ml of 1% TsOH in MeOH for 2 hours at room temperature, affording 47 mg (35%) of 13β-(1'-methylcyclopropanecarbonyloxy)milbemycin A$_4$.

$^1$H-NMR (300 MHz; CDCl$_3$; TMS): 1.33 ppm (s) (C$_1$'CH$_3$); 1.52 ppm (br.s) (C$_{14}$CH$_3$); 1.87 ppm (br. s) (C$_4$CH$_3$); 4.90 ppm (d, J=10.5 Hz) (C$_{13}$H).

EXAMPLE 2.14

Preparation of 13β-cyclobutanecarbonyloxymilbemycin D

At 0° C., 20.6 mg (0.174 mmol) of cyclobutanecarboxylic acid chloride in 0.5 ml of dichloromethane are cautiously added to a solution of 100 mg (0.145 mmol) of 5-O-tert-butyldimethylsilyl-13β-hydroxymilbemycin D in 2 ml of pyridine. The mixture is then worked up, and treatment of the crude product with 3 ml of a solution of 1% p-TsOH in MeOH for 2 hours at room temperature affords 45 mg (89%) of 13β-cyclobutanecarbonyloxymilbemycin D.

$^1$H-NMR (300 MHz; CDCl$_3$; TMS): 1.53 ppm (br.s) (C$_{14}$CH$_3$) 1.87 ppm (br. s) (C$_4$CH$_3$) 4.94 ppm (d, J=10.6 Hz) (C$_{13}$H).

EXAMPLE 2.15

Preparation of 13β-(2-adamantanecarbonyloxy)milbemycin D

A solution of 278 mg (0.40 mmol) of 5-O-tert-butyldimethylsilyl-15-hydroxy-Δ$^{13,14}$-milbemycin D, 367 mg (2.03 mmol) of 1-adamantanecarboxylic acid and 133 mg (0.82 mmol) of triethyl orthoacetate in 5 ml of absolute toluene is heated for 5 minutes to 100° C. in a flask equipped with a Claisen stillhead. Working up and chromatographic purification through 120 g of silica gel (elution with a 5:1 mixture of hexane and diethyl ether) affords 140 mg of 5-O-tert-butyldimethylsilyl-13β-1-adamantanecarbonyloxymilbemycin D. The silyl ether is treated with a solution of 3 ml of 1% TsOH in MeOH for 2 hours at room temperature, affording 113 mg (38%) of 13β-(1-adamantanecarbonyloxy)milbemycin D.

$^1$H-NMR (300 MHz; CDCl$_3$; TMS): 1.53 ppm (br.s) (C$_{14}$CH$_3$); 1.88 ppm (br. s) (C$_4$CH$_3$); 4.90 ppm (d, J=10.5 Hz) (C$_{13}$H).

EXAMPLE 2.16

Preparation of 13β-trichloroacryloyloxymilbemycin D

At 0° C., 44.0 mg (0.225 mmol) of trichloroacryloyl chloride in 0.5 ml of dichloromethane are cautiously added to a solution of 120 mg (0.175 mmol) of 5-O-tert-butyldimethylsilyl-13β-hydroxylmilbemycin D in 2 ml of dichloromethane. The mixture is then worked up, and treatment of the crude product with 3 ml of a solution of 1% p-TsOH in MeOH for 2 hours at room temperature affords 60 mg (47%) of 13β-trichloroacryloyloxymilbemycin D.

m.p. 160°–163° C.

$^1$H-NMR (300 MHz; CDCl$_3$; TMS): 1.54 ppm (br.s) (C$_{14}$CH$_3$); 1.87 ppm (br. s) (C$_4$CH$_3$); 5.04 ppm (d, J=10.6 Hz) (C$_{13}$H).

The following compounds of formula I for example may also be prepared in accordance with the procedures described above:

13β-(p-Chlorobenzoyloxy)milbemycin A$_4$:
IR $\nu_{max}^{KBr}$ cm$^{-1}$: 3470, 1720, 1595.
Mass spectrum (m/e): 696 (M$^+$), 568, 522.
$^1$H-NMR (270 MHz, CDCl$_3$, TMS) $\delta_{ppm}$: 3.97 (d, 1H, C$_6$H, J=6.2 Hz), 5.19 (d, 1H, C$_{13}$H, J=10.3 Hz), 7.42 (d, 2H, aromatic, J=8.8 Hz), 7.97 (d, 2H, aromatic, J=8.8 Hz).

13β-(p-Fluorophenoxyacetoxy)milbemycin A$_4$:
IR $\nu_{max}^{KBr}$ cm$^{-1}$: 3460, 1760, 1735, 1720.
Mass spectrum (m/e): 540 (M$^+$-170), 522, 504.
$^1$H-NMR (270 MHz, CDCl$_3$, TMS) $\delta_{ppm}$: 3.96 (d, 1H, C$_6$H, J=6.2 Hz), 4.59 (br. s, 2H, OCH$_2$COO), 5.05 (d, 1H, C$_{13}$H, J=10.6 Hz), 6.75–6.85 (m, 2H, aromatic), 6.9–7.05 (m, 2H, aromatic).

5-O-Acetyl-13β-formyloxymilbemycin A$_4$:
IR $\nu_{max}^{KBr}$ cm$^{-1}$: 3450, 1730
Mass spectrum (m/e): 628 (M$^+$), 570, 522, 458.
$^1$H-NMR (270 MHz, CDCl$_3$, TMS) $\delta_{ppm}$: 2.16 (s, 3H, OCOCH$_3$), 4.07 (d, 1H, C$_6$H, J=6.2 Hz), 5.05 (d, 1H, C$_{13}$H, J=10.3 Hz), 8.09 (s, 1H, OCHO).

13β-(p-[tert-butyl]benzoyloxy)milbemycin A$_4$
Mass spectrum (m/e): 718 (M$^+$), 700, 590, 540 522.
$^1$H-NMR (270 MHz, CDCl$_3$, TMS): 1.33 ppm (s) ((CH$_3$)$_3$CC$_6$H$_4$); 5.19 ppm (d, J=10 Hz) (C$_{13}$H); 7.35 ppm (d, J=9 Hz) (2H aromat.); 7.96 ppm (d, J=9 Hz) (2H aromat.).

13β-(3'-Chloropropionyloxy)milbemycin A₄
Mass spectrum (m/e): 648 (M+), 612, 540, 522.
¹H-NMR (270 MHz, CDCl₃, TMS): 2.80 ppm (t, J=7 Hz) (ClCH₂CH₂); 3.77 ppm (t, J=7 Hz) (ClCH₂CH₂); 5.00 ppm (d, J=10 Hz) (C₁₃H).

13β-Propionyloxymilbemycin A₄
Mass spectrum (m/e): 614 (M+) 540, 522, 486.
¹H-NMR (270 MHz, CDCl₃, TMS): 4.96 ppm (d, J=10 Hz) (C₁₃H).

13β-(3',3',3'-Trifluoropropionyloxy)milbemycin D:
¹H-NMR (250 MHz, CDCl₃, TMS): 3.17 ppm (q) (CF₃CH₂); 5.10 ppm (d, J=10 Hz) (C₁₃H).

13β-(3',3',3'-Trifluoropropionyloxy)milbemycin A₄:
¹H-NMR (300 MHz, CDCl₃, TMS): 3.15 ppm (q) (CF₃CH₂); 5.01 ppm (d, J=10 Hz) (C₁₃H).

13β-(2'-Chloro-3',3',3'-trifluoropropionyloxy)milbemycin D:
¹H-NMR (250 MHz, CDCl₃, TMS): 4.60 ppm (q) (CF₃CHCl); 5.02 ppm (d, J=10 Hz) (C₁₃H).

13β-Chloroacetylmilbemycin A₄:
¹H-NMR (300 MHz, CDCl₃, TMS): 4.06 ppm (s) (ClCH₂); 5.02 ppm (d, J=10 Hz) (C₁₃H).

The following compounds of formula I, listed together with compounds of the foregoing Examples, are also prepared in accordance with procedures analogous to those described:

TABLE 1

Typical representatives of compounds of formula I wherein $R_1$ is hydrogen.

| Comp. | $R_2$ | R |
|---|---|---|
| 1.1 | CH₃ | H |
| 1.2 | C₂H₇ | H |
| 1.3 | isoC₃H₇ | H |
| 1.4 | sec-C₄H₉ | H |
| 1.5 | CH₃ | CH₃ |
| 1.6 | C₂H₅ | CH₃ |
| 1.7 | isoC₃H₇ | CH₃ |
| 1.8 | sec-C₄H₉ | CH₃ |
| 1.9 | CH₃ | C(CH₃)₃ |
| 1.10 | C₂H₅ | C(CH₃)₃ |
| 1.11 | isoC₃H₇ | C(CH₃)₃ |
| 1.12 | sec-C₄H₉ | C(CH₃)₃ |
| 1.13 | CH₃ | CH₃OCH₂ |
| 1.14 | C₂H₅ | CH₃OCH₂ |
| 1.15 | isoC₃H₇ | CH₃OCH₂ |
| 1.16 | sec-C₄H₉ | CH₃OCH₂ |
| 1.17 | CH₃ | CH₃OC(CH₃)₂ |
| 1.18 | C₂H₅ | CH₃OC(CH₃)₂ |
| 1.19 | isoC₃H₇ | CH₃OC(CH₃)₂ |
| 1.20 | sec-C₄H₉ | CH₃OC(CH₃)₂ |
| 1.21 | CH₃ | (CH₃)₂CH |
| 1.22 | C₂H₅ | (CH₃)₂CH |
| 1.23 | isoC₃H₇ | (CH₃)₂CH |
| 1.24 | sec-C₄H₉ | (CH₃)₂CH |
| 1.25 | CH₃ | CCl₃ |
| 1.26 | C₂H₅ | CCl₃ |
| 1.27 | isoC₃H₇ | CCl₃ |
| 1.28 | sec-C₄H₉ | CCl₃ |
| 1.29 | CH₃ | CF₃ |
| 1.30 | C₂H₅ | CF₃ |
| 1.31 | isoC₃H₇ | CF₃CHCl |
| 1.32 | sec-C₄H₉ | CF₃ |
| 1.33 | CH₃ | C(Cl₃)CHCl |
| 1.34 | C₂H₅ | C(Cl₃)CHCl |
| 1.35 | isoC₃H₇ | CF₃CH₂ |
| 1.36 | sec-C₄H₉ | C(Cl₃)CHCl |
| 1.37 | CH₃ | ClCH₂CH₂CH₂ |
| 1.38 | C₂H₅ | ClCH₂CH₂CH₂ |
| 1.39 | isoC₃H₇ | ClCH₂CH₂CH₂ |
| 1.40 | sec-C₄H₉ | ClCH₂CH₂CH₂ |
| 1.41 | CH₃ | CH₂=CH |
| 1.42 | C₂H₅ | CH₂=CH |
| 1.43 | isoC₃H₇ | CH₂=CH |
| 1.44 | sec-C₄H₉ | CH₂=CH |
| 1.45 | CH₃ | CH₂=CH—CH₂ |
| 1.46 | C₂H₅ | CH₂=CH—CH₂ |
| 1.47 | isoC₃H₇ | CH₂=CH—CH₂ |
| 1.48 | sec-C₄H₉ | CH₂=CH—CH₂ |
| 1.49 | CH₃ | CH≡C—CH₂ |
| 1.50 | C₂H₅ | CH≡C—CH₂ |
| 1.51 | isoC₃H₇ | CH≡C—CH₂ |
| 1.52 | sec-C₄H₉ | CH≡C—CH₂ |
| 1.53 | CH₃ | (CH₃)₂C=CH |
| 1.54 | C₂H₅ | (CH₃)₂C=CH |
| 1.55 | isoC₃H₇ | (CH₃)₂C=CH |
| 1.56 | sec-C₄H₉ | (CH₃)₂C=CH |
| 1.57 | CH₃ | (Cl)₂C=C(Cl) |
| 1.58 | C₂H₅ | (Cl)₂C=C(Cl) |
| 1.59 | isoC₃H₇ | (Cl)₂C=C(Cl) |
| 1.60 | sec-C₄H₉ | (Cl)₂C=C(Cl) |
| 1.61 | CH₃ | CF₃CCl₂ |
| 1.62 | C₂H₅ | CF₃CCl₂ |
| 1.63 | isoC₃H₇ | CF₃CCl₂ |
| 1.64 | sec-C₄H₉ | CF₃CCl₂ |
| 1.65 | CH₃ | cyclopropyl |
| 1.66 | C₂H₅ | cyclopropyl |
| 1.67 | isoC₃H₇ | cyclopropyl |
| 1.68 | sec-C₄H₉ | cyclopropyl |
| 1.69 | CH₃ | 2,2-dimethyl-cyclopropyl |
| 1.70 | C₂H₅ | 2,2-dimethyl-cyclopropyl |
| 1.71 | isoC₃H₇ | 2,2-dimethyl-cyclopropyl |
| 1.72 | sec-C₄H₉ | 2,2-dimethyl-cyclopropyl |
| 1.73 | CH₃ | 2,2-dimethyl-3-(2,2-dichlorovinyl)cyclopropyl |
| 1.74 | C₂H₅ | 2,2-dimethyl-3-(2,2-dichlorovinyl)cyclopropyl |
| 1.75 | isoC₃H₇ | 2,2-dimethyl-3-(2,2-dichlorovinyl)cyclopropyl |
| 1.76 | sec-C₄H₉ | 2,2-dimethyl-3-(2,2-dichlorovinyl)cyclopropyl |
| 1.77 | CH₃ | cyclobutyl |
| 1.78 | C₂H₅ | cyclobutyl |
| 1.79 | isoC₃H₇ | cyclobutyl |
| 1.80 | sec-C₄H₉ | cyclobutyl |
| 1.81 | CH₃ | cyclohexyl |
| 1.82 | C₂H₅ | cyclohexyl |
| 1.83 | isoC₃H₇ | cyclohexyl |
| 1.84 | sec-C₄H₉ | cyclohexyl |
| 1.85 | CH₃ | phenyl |
| 1.86 | C₂H₅ | phenyl |
| 1.87 | isoC₃H₇ | phenyl |
| 1.88 | sec-C₄H₉ | phenyl |
| 1.89 | CH₃ | p-chlorophenyl |
| 1.90 | C₂H₅ | p-chlorophenyl |
| 1.91 | isoC₃H₇ | p-chlorophenyl |
| 1.92 | sec-C₄H₉ | p-chlorophenyl |
| 1.93 | CH₃ | p-tolyl |
| 1.94 | C₂H₅ | p-tolyl |
| 1.95 | isoC₃H₇ | p-tolyl |
| 1.96 | sec-C₄H₉ | p-tolyl |
| 1.97 | CH₃ | p-nitrophenyl |
| 1.98 | C₂H₅ | p-nitrophenyl |
| 1.99 | isoC₃H₇ | p-nitrophenyl |
| 2.00 | sec-C₄H₉ | p-nitrophenyl |
| 2.1 | CH₃ | n-hexyl |
| 2.2 | C₂H₅ | n-hexyl |
| 2.3 | isoC₃H₇ | n-hexyl |
| 2.4 | sec-C₄H₉ | n-hexyl |
| 2.5 | CH₃ | ClCH₂C(CH₃)₂ |
| 2.6 | C₂H₅ | ClCH₂C(CH₃)₂ |
| 2.7 | isoC₃H₇ | ClCH₂C(CH₃)₂ |
| 2.8 | sec-C₄H₉ | ClCH₂C(CH₃)₂ |
| 2.9 | CH₃ | 1-methylcyclopropyl |
| 2.10 | C₂H₅ | 1-methylcyclopropyl |
| 2.11 | isoC₃H₇ | 1-methylcyclopropyl |
| 2.12 | sec-C₄H₉ | 1-methylcyclopropyl |
| 2.13 | CH₃ | adamantyl |

TABLE 1-continued

Typical representatives of compounds of formula I wherein $R_1$ is hydrogen.

| Comp. | $R_2$ | R |
|---|---|---|
| 2.14 | $C_2H_5$ | adamantyl |
| 2.15 | iso$C_3H_7$ | adamantyl |
| 2.16 | sec-$C_4H_9$ | adamantyl |
| 2.17 | $C_2H_5$ | p-fluorophenoxymethyl |
| 2.18 | $C_2H_5$ | $ClC(CH_3)_2$ |
| 2.19 | $C_2H_5$ | $CH_3CCl_2$ |
| 2.20 | $C_2H_5$ | $CH_3CH_2C(CH_3)_2$ |
| 2.21 | $C_2H_5$ | $C(CH_3)_3CH_2$ |
| 2.22 | $C_2H_5$ | $C(CH_3)_3C(CH_3)_2$ |
| 2.23 | $C_2H_5$ | $ClCH_2$ |
| 2.24 | $C_2H_5$ | $CF_3CH_2$ |
| 2.25 | $C_2H_5$ | 1-methylcyclobutyl |
| 2.26 | $C_2H_5$ | 1-methylcyclopentyl |
| 2.27 | $C_2H_5$ | $FCH_2C(CH_3)_2$ |
| 2.28 | $C_2H_5$ | $CH_2=C(CH_3)$ |
| 2.29 | $C_2H_5$ | $ClCH_2CH_2$ |
| 2.30 | $C_2H_5$ | p-(tert-$C_4H_9$)phenyl |
| 2.31 | $C_2H_5$ | $CH_3CH_2CH_2$ |
| 2.32 | $C_2H_5$ | $CH_3CH_2$ |

The contents of this Table are illustrative and constitute no limitation.

Formulation Examples for active ingredients for formula I (throughout, percentages are by weight)

| Wettable powders | (a) | (b) | (c) |
|---|---|---|---|
| compound of Table 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly despersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
|---|---|
| compound of Table 1 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| compound of Table 1 | 5% | 8% |
| talcum | 95% | — |
| kaolin | — | 92% |

Ready for use dusts are obtained by mixing the active ingredient with the carrier, and grinding the mixture in a suitable mill.

| Extruder granulate | |
|---|---|
| compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or pellets | |
|---|---|
| I compound of Table 1 | 33.00% |
| methyl cellulose | 0.80% |
| highly dispersed silicic acid | 0.80% |
| maize starch | 8.40% |

The methyl cellulose is stirred in water and allowed to swell. Then the silicic acid is stirred in to give a homogeneous suspension. The compound of formula I and the maize starch are mixed and the aqueous suspension is added to the mix, which is kneaded to a paste. This paste is granulated through a 12M sieve and the granulate is dried.

| II crystalline lactose | 22.50% |
|---|---|
| maize starch | 17.00% |
| microcrystalline cellulose | 16.50% |
| magnesium stearate | 1.00% |

All 4 adjuvants are thoroughly mixed. Phases I and II are mixed and compressed to tablets or pellets.

If the compounds of formula I, or compositions containing them, are used for controlling endoparasitic nematodes, cestodes and trematodes in domestic animals and productive livestock, for example cattle, sheep, goats, cats and dogs, they can be administered to the animals in both single and repeated doses. Depending on the species of animal, the individual doses are preferably administered in amounts ranging from 0.1 to 10 mg/kg of body weight. A better action is often achieved by protracted administration, or lower total doses will also suffice. The compounds, or compositions containing them, can also be added to feeds and drinks. The ready-prepared feeds contain the active ingredients preferably in a concentration of 0.005 to 0.1 percent by weight. The compositions can be administered to the animals perorally in the form of solutions, emulsions, suspensions, powders, tablets, pellets, boluses or capsules.

If the physical and toxicological properties of solutions or emulsions permit it, the compounds of formula I, or compositions containing them, can also be injected into animals for example subcutaneously, administered intraruminally or applied to the bodies of the animals by the pour-on method. Administration by means of salt licks or molasses blocks is also possible.

BIOLOGICAL EXAMPLES

1. Insecticidal stomach poison action against *Spodoptera littoralis*

Potted cotton plants in the 5-leaf stage are sprayed with a solution containing 1, 3, 12.5 or 50 ppm of the test compound in acetone/water. After the coating has dried, the plants are populated with about 30 larvae ($L_1$ stage) of *Spodoptera littoralis*. Two plants are used for each test compound and test species. The test is carried out at about 24° C. and 60% relative humidity. Evaluations and intermediate evaluations of moribund insects, larval growth and feeding damage are made after 24, 48 and 72 hours. The compounds of formula I effect complete kill at a concentration of 3 ppm after 24 hours. Compounds 1.7, 1.10, 1.31, 1.35, 1.79, 2.6, 2.7 and 2.11 are particularly effective.

2. Action against plant-destructive acarids: OP-sensitive *Tetranychus urticae*

16 hours before the start of the test, the primary leaves of bean plants (*Phaseolus vulgaris*) are infected with an infested piece of leaf from a mass culture of *Tetranychus urticae*. Upon removal of the piece of leaf, the plants infested with all stages of the mites are sprayed to drip point with a solution containing 0.2 ppm, 0.4 ppm or 1.6 ppm of the test compound. The temperature in the greenhouse compartment is about 25° C. The percentage of mobile stages (adults and nymphs) and of eggs is evaluated under a stereoscopic microscope after 7 days. The compounds of formula I effect complete kill at 0.4 ppm. Compounds 1.11. and 2.11 are particularly effective.

3. Action against L₁ larvae of *Lucilia sericata*

1 ml of an aqueous suspension of test compound is mixed with 3 ml of a special larval culture medium at about 50° C. such that a homogeneous composition containing 250 ppm or 100 ppm is obtained. About 30 *Lucilia sericata* larvae (L₁) are put into each test tube containing active ingredient. A mortality count is made after 4 days. The compounds of formula I effect complete kill at 250 ppm. Complete kill is effected at 100 ppm by compounds 1.10, 1.11, 1.31, 1.39, 1.59, 1.67, 1.75, 1.79, 1.90, 2.3, 2.7, 2.10, 2.11 and 2.15.

4. Acaricidal action against *Boophilus microplus* (Biarra strain)

Adhesive tape is applied vertically across a PVC plate so that 10 fully replete female *Boophilus microplus* ticks (Biarra strain) can be affixed thereto with their backs, side by side, in a row. Each tick is injected from an injection needle with 1 μl of a liquid which contains a 1:1 mixture of polyethylene glycol and acetone, in which mixture a specific amount of test compound of 1, 0.5, 0.1 or 0.01 μg per tick is dissolved. Control ticks are injected with liquid containing no test compound. After this treatment, the ticks are detached from the support and kept under normal conditions in an insectarium at about 28° C. and 80% relative humidity until oviposition has taken place and the larvae have hatched from the eggs of the control ticks. The activity of the test compound is determined with the IR₉₀, i.e. the effective dose is determined at which 9 out of 10 female ticks (90%) even after 30 days lay eggs from which larvae are unable to hatch.

The compounds of formula I achieve an IR₉₀ of 0.5 μg. Compounds 1.3, 1.7, 1.10, 1.11, 1.59, 1.75 and 2.7 are particularly effective.

5. Trial with sheep infected with nematodes (*Haemonchus concortus* and *Trichostrongylus colubriformis*)

The test compound is administered in the form of a suspension with a stomach probe or by intraruminal injection to sheep which have been artificially infected with *Haemonchus concortus* and *Trichostrongylus colubriformis*. 1 to 3 animals are used for each dose. Each sheep is treated only once with a single dose of 0.5 mg/kg of body weight. Evaluation is made by comparing the number of worm eggs excreted in the faeces of the sheep before and after treatment.

Untreated sheep infected simultaneously and in the same manner are used as controls. In comparison with untreated and infected control groups, there is no nematode infestation (=complete reduction of the number of worm eggs in the faeces) in sheep which have been treated with one of the compounds of formula I at 0.5 mg/kg. Compounds 1.10, 1.11, 1.31, 2.7 and 2.11 are particularly effective.

6. Contact action against *Aphis craccivora*

Pea plantlets which have been infested with all development stages of the aphid are sprayed with a solution prepared from an emulsifiable concentrate of the test compound and containing 50 ppm, 25 ppm or 12.5 ppm of active ingredient. After 3 days evaluation is made to establish whether at least 80% of the aphids are dead or have dropped from the plants. A composition is only rated as effective at this level of activity.

Complete kill (100%) is achieved with compounds of formula I at a concentration of 12.5 ppm. Compounds 1.10, 1.11, 1.39, 1.75, 1.79, 2.3, 2.6, 2.7, 2.11 and 2.15 are particularly effective.

7. Larvicidal action against *Aedes aegypti*

A 0.1% solution of the test compound in acetone is pipetted onto the surface of 150 ml of water in beakers in amounts sufficient to give concentrations of 10 ppm, 3.3 ppm and 1.6 ppm. After the acetone has evaporated, 30 to 40 three-day-old larvae of *Aedes aegypti* are put into each beaker. Mortality counts are made after 1, 2 and 5 days.

In this test, the compounds of formula I effect complete kill of all larvae at a concentration of 1.6 ppm after 1 day. Compounds 1.11, 1.31, 1.35, 1.39, 1.59, 1.67, 1.75, 1.79, 2.3, 2.6, 2.7, 2.10, 2.11 and 2.15 are particularly effective.

What is claimed is:

1. A 13β-substituted compound of the formula:

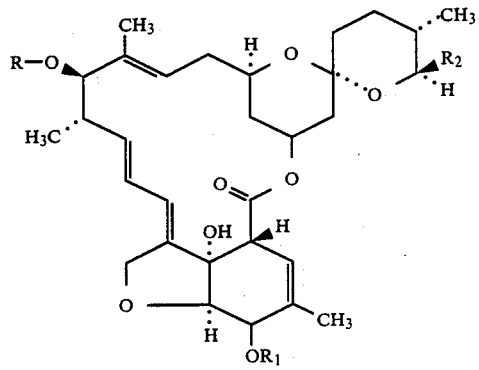

wherein:
R is pivaloyl;
R₁ is hydrogen; alkanoyl of 2 to 11 carbon atoms, unsubstituted or substituted with halo; benzoyl, unsubstituted or substituted by halo, alkyl of 1 to 3 carbon atoms, haloalkyl of 1 to 3 carbon atoms, alkoxy of 1 to 3 carbon atoms, haloalkoxy of 1 to 3 carbon atoms, cyano, or nitro; or phenylacetyl, unsubstituted or substituted by halo, alkyl of 1 to 3 carbon atoms, haloalkyl of 1 to 3 carbon atoms, alkoxy of 1 to 3 carbon atoms, haloalkoxy of 1 to 3 carbon atoms, cyano, or nitro; and
R₂ is methyl, ethyl, isopropyl, or sec.-butyl.

2. A 13β-substituted compound according to claim 1 wherein R₁ is hydrogen.

3. A 13β-substituted compound according to claim 1 wherein $R_2$ is ethyl or isopropyl.

4. The 13β-substituted compound according to claim 1 which is 13β-pivaloyloxymilbemycin $A_4$.

5. The 13β-substituted compound according to claim 1 which is 13β-pivaloyloxymilbemycin D.

6. A composition for controlling pests which comprises an effective amount of at least one 13β-substituted compound according to claim 1 in combination with at least one carrier or dispersing agent.

7. A method of controlling pests which comprises applying or administering to an animal or applying to a plant or the loci of the pests, an effective amount of at least one 13β-substituted compound according to claim 1.

* * * * *